(12) United States Patent
Pan

(10) Patent No.: US 9,784,687 B2
(45) Date of Patent: Oct. 10, 2017

(54) EXAMINATION METHOD TO APPRAIS CORUNDUM THAT HAS UNDERGONE BERYLLIUM DIFFUSION TREATMENT

(71) Applicant: Dong-Shyogn Pan, Taipei (TW)

(72) Inventor: Dong-Shyogn Pan, Taipei (TW)

( * ) Notice: Subject to any disclaimer, the term of this patent is extended or adjusted under 35 U.S.C. 154(b) by 71 days.

(21) Appl. No.: 14/838,376

(22) Filed: Aug. 28, 2015

(65) Prior Publication Data

US 2016/0109373 A1    Apr. 21, 2016

Related U.S. Application Data

(60) Provisional application No. 62/065,619, filed on Oct. 18, 2014.

(51) Int. Cl.
| | |
|---|---|
| G01N 21/00 | (2006.01) |
| G01N 21/87 | (2006.01) |
| G01J 3/44 | (2006.01) |
| G01N 21/65 | (2006.01) |

(52) U.S. Cl.
CPC ............ G01N 21/87 (2013.01); G01J 3/44 (2013.01); *G01N 21/65* (2013.01)

(58) Field of Classification Search
CPC ........ G01N 21/87; G01N 21/65; G01N 33/68; G01N 33/58; G01N 33/6845; A61K 47/32; G01J 3/44; G01J 3/30
See application file for complete search history.

(56) References Cited

U.S. PATENT DOCUMENTS

| | | | |
|---|---|---|---|
| 6,987,564 B2 * | 1/2006 | Gornushkin | G01J 3/44 356/301 |
| 7,557,917 B1 * | 7/2009 | Beesley | G01N 21/87 356/30 |
| 2014/0043607 A1 * | 2/2014 | Wang | G01N 21/65 356/301 |
| 2014/0243428 A1 * | 8/2014 | Varghese | A61K 47/32 514/772.6 |
| 2015/0192590 A1 * | 7/2015 | Sodeoka | G01N 21/65 435/6.1 |

* cited by examiner

*Primary Examiner* — Jamil Ahmed

(57) ABSTRACT

This invention is within the technical field of corundum appraisal, and it involves an examination method to determine whether corundum has undergone beryllium diffusion treatment. Procedurally, a highly sensitive Raman spectrometer (S/N>10,000) is used to scan and examine the samples. The spectrometer is fitted with a tailor-made probe having a large facula and surface area. Specially developed software is then used to perform an intensity correction and a background elimination to obtain a specific Raman spectral range (250-120 cm-1) with the corrected intensity and a smooth baseline. The corrected and standardized Raman characteristic peak at 804 cm-1 (side-band) is used as a basis to determine whether the corundum has undergone beryllium diffusion treatment. This invention method has the advantages of being non-destructive, simple, fast, and practical. Also, it can accurately determine whether corundum has been treated.

1 Claim, 2 Drawing Sheets

EXAMINATION METHOD TO APPRAIS CORUNDUM THAT HAS UNDERGONE BERYLLIUM DIFFUSION TREATMENT

RELATED APPLICATIONS

This application claims priority benefit of U.S. Provisional Patent Application No. 62/065,619 filed 18 Oct. 2014, of which is hereby incorporated by reference.

BACKGROUND OF THE INVENTION

1. Field of the Invention

The present invention relates to a non-destructive examination method to determine whether corundum has undergone beryllium diffusion treatment.

2. Related Art

Natural corundum is one of the three precious gems in the world, and high-quality corundum is expensive. Over a decade ago, corundum that had undergone beryllium diffusion treatment entered the market, creating much confusion in the pricing system of corundum. Currently, among the techniques used for the appraisal of treated corundum, the main approach is analysis using chemical elements (LIBS, ICP-MS). The beryllium content can be examined using this method, providing a basis for determining whether beryllium diffusion treatment has been performed. However, the use of chemical elements has the disadvantages of incurring high costs and being destructive. A non-destructive and rapid method to determine whether corundum has been treated is needed to solve the existing technical problems.

SUMMARY OF THE INVENTION

Accordingly, an object of the present invention is to provide a simple yet intuitive signal of the characteristic peak of the Raman spectra for a rapid examination method to appraise whether corundum has been treated.

To achieve the above-mentioned object, the examination method to appraise corundum that has undergone beryllium diffusion treatment, comprises providing a Raman spectrometer having a laser beam of wavelength 785 nm and total laser power of 450 mw; three continuous scans being performed using a probe with a large facula and surface area to obtain three spectra, from which an average Raman spectra is determined; defining a collection range of the spectrometer as 250-1200 $cm^{-1}$; and after the collection of the Raman spectral data, the intensity being subjected to two operations: (a) correction and standardization, and (b) background elimination that result in a Raman spectrogram with a smooth baseline and enhanced intensity; wherein Raman characteristic peaks for natural corundum occur at 375, 412, 572, 640, and 745 $cm^{-1}$, whereas treated corundum has an extra Raman characteristic peak with a raised baseline at 804 $cm^{-1}$.

DESCRIPTION OF THE PREFERRED EMBODIMENTS

A simple yet intuitive signal of the characteristic peak of the Raman spectra for a rapid examination method to appraise whether corundum has been treated. The procedures comprising the technique are detailed below and illustrated in FIGS. 1 and 2.

The examination method comprises: providing a Raman spectrometer which is highly sensitive (S/N>10,000) and has a laser beam of wavelength 785 nm and total laser power of 450 mw; three continuous scans being performed using a probe with a large facula and surface area to obtain three spectra, from which an average Raman spectra is determined; defining a collection range of the spectrometer as 250-1200 $cm^{-1}$; and after the collection of the Raman spectral data, the intensity being subjected to two operations: (a) correction and standardization, and (b) background elimination that result in a Raman spectrogram with a smooth baseline and enhanced intensity; wherein Raman characteristic peaks for natural corundum occur at 375, 412, 572, 640, and 745 $cm^{-1}$, whereas treated corundum has an extra Raman characteristic peak with a raised baseline at 804 $cm^{-1}$.

Figure 1:
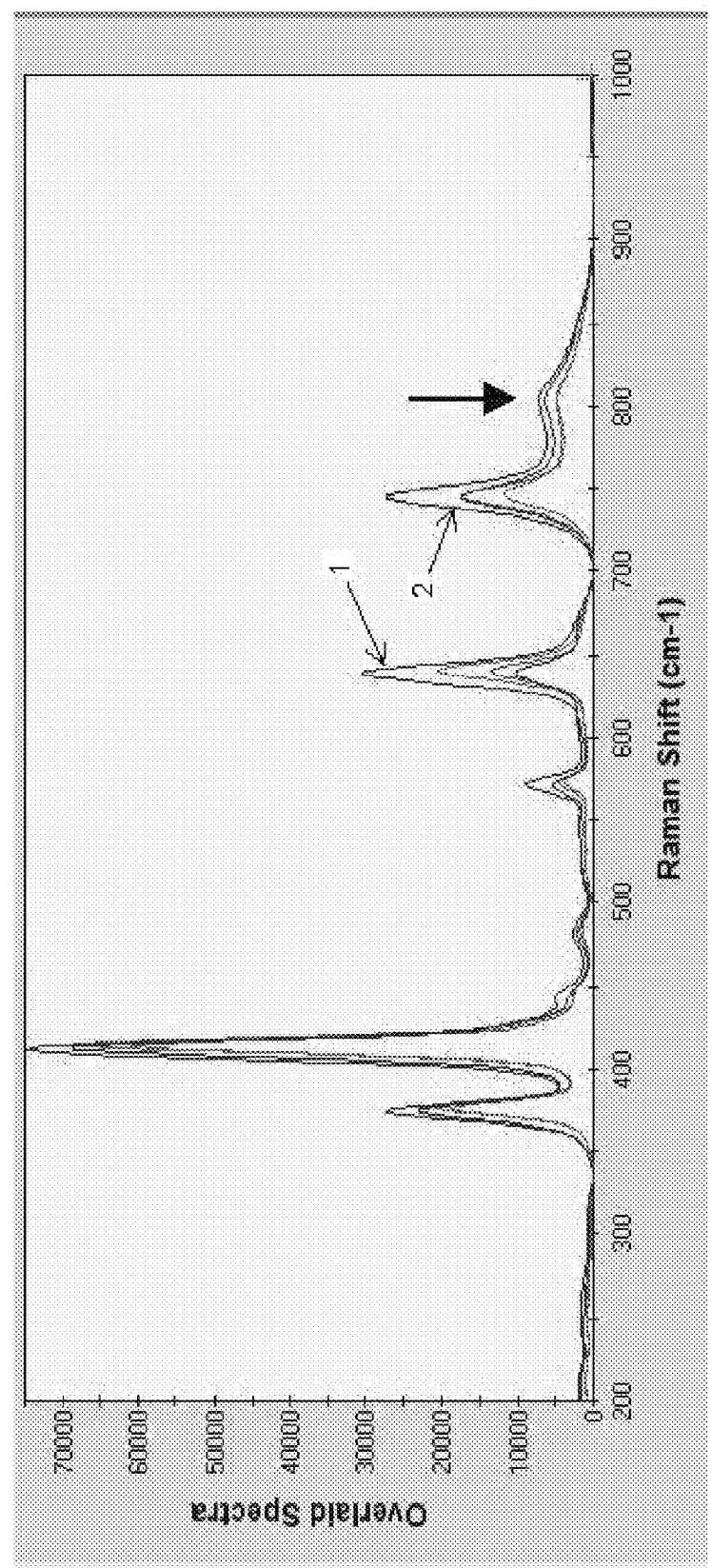
FIG. 1 is a schematic chart illustrating Raman spectra of beryllium diffused corundum of the present invention.
Figure 2:
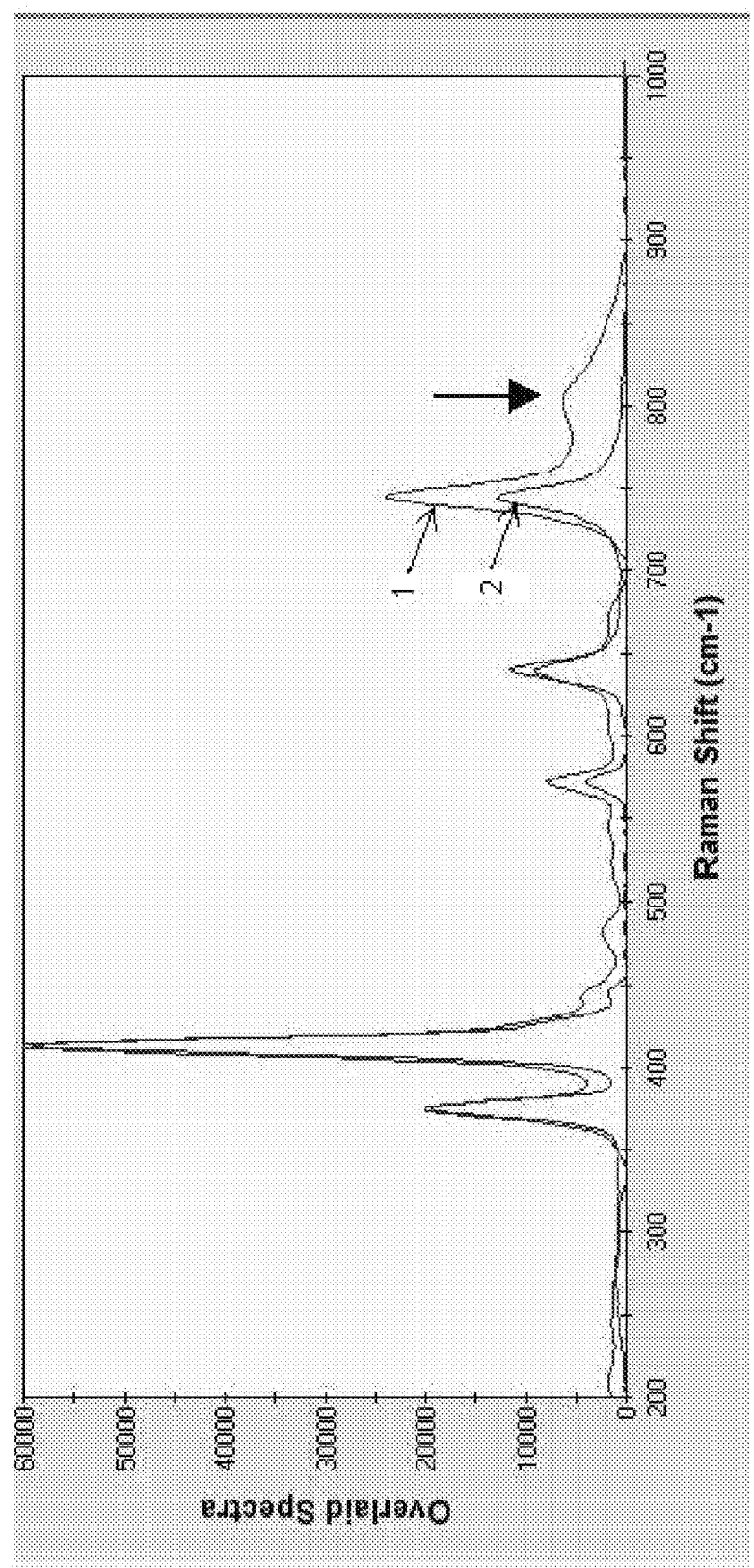
FIG. 2 is a schematic chart illustrating overlaid Raman spectra for natural and beryllium treated corundum.

As shown in FIGS. 1 and 2, the Raman characteristic peak at 804 $cm^{-1}$ (side-band) is indicated by a bold arrow. FIG. 2 is a schematic chart illustrating overlaid Raman spectra for natural and beryllium treated corundum. It is noted that the Raman spectrum for the corundum that has undergone beryllium diffused treatment is indicated by a first line 1, and that for the natural corundum is indicated by a second line 2. The presence of the Raman characteristic peak at 804 $cm^{-1}$ (side-band) with a raised baseline can be used to determine whether the corundum has been treated.

Under the proposed method, the Raman spectra of dozens of treated corundum samples were collected (FIG. 1). These were overlaid onto the Raman spectra of natural corundum for comparison (FIG. 2). The Raman peak at 804 $cm^{-1}$ (side-band) does not appear for the natural corundum. Thus, it can be used as a basis to appraise whether the corundum has been treated.

The use of the Raman spectra in the proposed invention method has the following advantages: it is non-destructive, there is no requirement for pre-processing, and it allows a rapid analysis. The method can be used to determine whether corundum has undergone beryllium diffusion treatment and is summarized as follows:

(a) The presence of a Raman characteristic peak is used as an indicator that the corundum has been treated. It is a scientific, impartial, and objective appraisal method.

(b) This method can be applied for the appraisal of both loose and inlaid corundum and can be used on corundum samples of all sizes.

(c) Specially developed software and standard samples were used to perform the correction and standardization, as well as the baseline processing. This reduces the slight differences in the intensities of the Raman peaks of the corundum samples between analyses, thereby ensuring data consistency for each analysis.

It is understood that the invention may be embodied in other forms within the scope of the claims. Thus the present examples and embodiments are to be considered in all respects as illustrative, and not restrictive, of the invention defined by the claims.

What is claimed is:

1. An examination method to appraise corundum that has undergone beryllium diffusion treatment, comprising:
   providing a Raman spectrometer having a laser beam of wavelength 785 nm and total laser power of 450 mw;

three continuous scans being performed using a probe with a large facula and surface area to obtain three spectra, from which an average Raman spectra is determined;

defining a collection range of the spectrometer as 250-1200 $cm^{-1}$; and after the collection of the Raman spectral data, the intensity being subjected to two operations: (a) correction and standardization, and (b) background elimination that result in a Raman spectrogram with a smooth baseline and enhanced intensity;

wherein Raman characteristic peaks for natural corundum occur at 375, 412, 572, 640, and 745 $cm^{-1}$, whereas treated corundum has an extra Raman characteristic peak with a raised baseline at 804 $cm^{-1}$.

* * * * *